United States Patent [19]

Oga et al.

[11] 4,221,723
[45] Sep. 9, 1980

[54] METHOD OF PREPARING COMENIC ACID

[75] Inventors: Shiyunichiro Oga; Kazuo Asano, both of Ibaraki; Katsumi Imada, Kyoto, all of Japan

[73] Assignee: Daiichi Seiyaku Company, Ltd., Tokyo, Japan

[21] Appl. No.: 706,367

[22] Filed: Jul. 19, 1976

Related U.S. Application Data

[63] Continuation of Ser. No. 208,872, Dec. 16, 1976, abandoned, which is a continuation-in-part of Ser. No. 784,171, Dec. 16, 1968, abandoned.

[51] Int. Cl.$^2$ ............................................. C07D 309/38
[52] U.S. Cl. ............................................... 260/345.7 R
[58] Field of Search ...................... 260/345.7, 345.7 R

[56] References Cited

U.S. PATENT DOCUMENTS 3,654,316   4/1972   Oga et al. ........................... 260/345.7

FOREIGN PATENT DOCUMENTS 1814341   7/1969   Fed. Rep. of Germany ........ 260/345.7

Primary Examiner—Nicky Chan
Attorney, Agent, or Firm—Sughrue, Rothwell, Mion, Zinn and Macpeak

[57] ABSTRACT

Preparing comenic acid by heating 2,5-diketo-gluconic acid at a temperature within the range of 8°–120° C. and at a pH below 0.1. α-pyrone derivatives are formed as by-products, and comenic acid is separated therefrom by utilizing the solubility differences between the α-pyrone derivatives and comenic acid.

4 Claims, 1 Drawing Figure

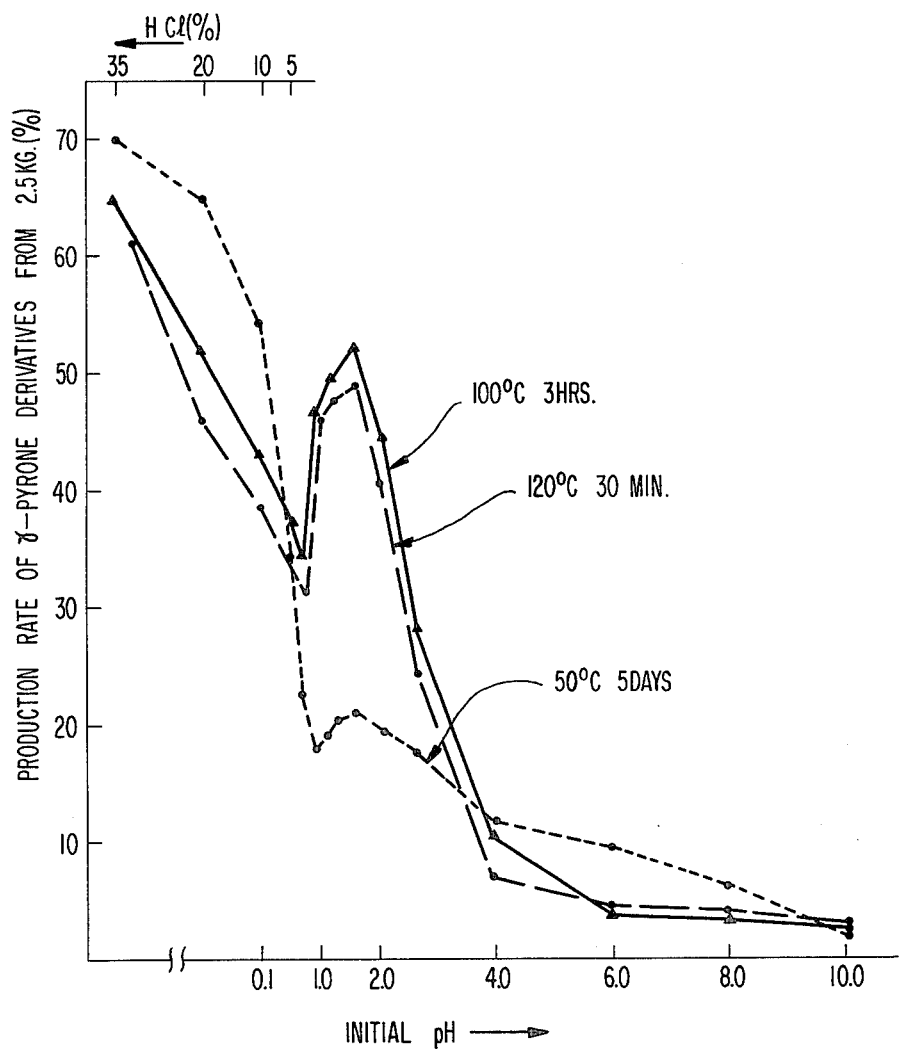

METHOD OF PREPARING COMENIC ACID

CROSS-REFERENCE TO RELATED APPLICATIONS

This is a continuation of application Ser. No. 208,872, filed Dec. 16, 1976 now abandoned which, in turn is a continuation-in-part application of our co-pending application U.S. Ser. No. 784,171, filed on Dec. 16, 1968, now abandoned.

BACKGROUND OF THE INVENTION

1. Field of the Invention

The present invention relates to a novel improvement in the method for preparing comenic acid (5-hydroxy-2-carboxy-4-pyrone), and more particularly to an improvement in the process for preparing comenic acid from 2,5-diketo-gluconic acid or its metal salt and for obtaining comenic acid from the resultant reaction mixture, in substantially appreciable yields, greater than that obtained in our co-pending application noted above.

2. Description of the Prior Art

Few reports deal with the preparation of comenic acid. For instance, Aida et al reported that the presence of comenic acid, rubiginic acid and rubiginol was confirmed by the paper chromatography of an incubated solution of 2,5-diketo-gluconic acid with Gluconoacetobacter liquefaciens and a phosphoric buffer. (Aida et al; Bulletin of the Agricultural Chemical Society of Japan 21 30-37 (1957)). Moreover, they reported that comenic acid and other γ-pyrone derivatives were produced by the fermentation of Gluconacetobacter liquefaciens in a medium containing glucose (9.3%), yeast extract (0.8%), and calcium carbonate (2.5%) for ten days. (Aida et al; Bulletin Agricultural Chemical Society, Japan 19, 97 (1955)). The latter fermentation method however, is of no avail for manufacturing comenic acid because of its poor yield (e.g., only 0.5 g. comenic acid is obtained from 100 g. of glucose by the fermentation).

On the hand, the chemical methods have been known. Chemical procedures involve the oxidation of kojic acid of the decarboxylation of meconic acid. These methods are not economical because the starting materials are very expensive.

SUMMARY OF THE INVENTION

Comenic acid may be produced by heating an aqueous solution of 2,5-diketo-gluconic acid at a temperature within the range of 8°–120° C. and at a pH of below 0.1. (reference to this acid is intended to include its metal salts, such as Ca, K, Na, Mg an the like). Comenic acid can be easily separated from the reaction mixture which contains α-pyrone derivatives by recrystallization from water utilizing the solubility differences between comenic acid and the γ-pyrone derivatives.

An object of the present invention is thus to provide a novel and valuable process for producing comenic acid which is useful of the preparations of maltol, a food additive useful as a flavor.

DETAILED DESCRIPTION OF THE INVENTION

It has been found as a result of experimentation by the inventors that 2,5-diketo-gluconic acid may be primarily converted to comenic acid and to other γ-pyrone derivatives in extremely high yields. The reaction proceeds from 2,5-diketo-gluconic acid (I) to comenic acid (II) as the result of dehydration and a rearrangement reaction as shown in the following scheme.

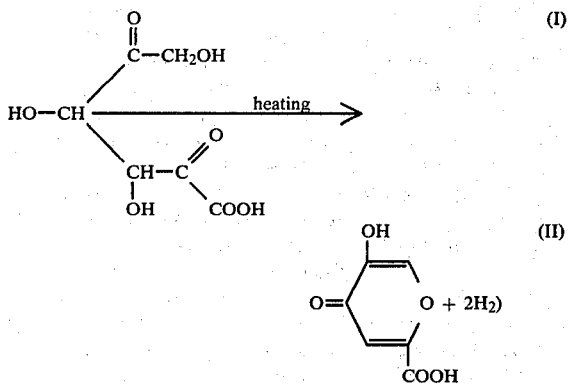

In accordance with the present invention, comenic acid (II) is economically produced by heating an aqueous solution of 2,5-diketo-gluconic acid (I) at a pH of below 0.1. The comenic acid can be separated in good yields from the reaction mixture along with other γ-pyrone derivatives produced as by-products.

The starting material used in the present invention, namely, 2,5-diketo-gluconic acid (I), is easily produced as a metabolite by known preparation methods, such as the fermentation of Gluconobacter melanogenum MA 6.2 and/or oxidative bacteria belonging to Gluconoacetobacter liquefaciens, in a glucose medium. (Katynelsn et al, J. Biol. Chem. 204, 43 (1953); Aida et al, Bulletin Agriculture Chemical Society, Japan 21, 30, 37 (1957)).

According to the present invention, comenic acid (II) is produced by heating a 1–30% (preferably 5–15%) aqueous solution of 2,5-diketo-gluconic acid (I) which may be a fermentation liquor which contains 2,5-diketo-gluconic acid (I) at a temperature of 8°–120° C. The perferred temperature range is from 50° C.–60° C., and the pH of the reaction solution containing 2,5-diketo-gluconic acid (I) is below 0.1. Thus, the gluconic acid (I) is converted to various γ-pyrone derivatives.

It was found that 2,5-diketo-gluconic acid (I) was converted at a 20% greater yield into γ-pyrone derivatives in the presence of an alkaline earth metal carbonate, such as calcium carbonate or barium carbonate, in the reaction solution (in comparison with the case without those salts of the alkaline earth metals). The existence of a trace of iron- (ferrous and ferric), nickel-, or cobalt-salts and mixtures thereof in the solution also affected the reaction in a favorable manner, illustrating a catalytic effect, though the reason why these metal ions work effectively has not been determined.

A large amount of comenic acid and small amounts of other γ-pyrone derivatives, as rubiginic acid, pyromeconic acid, rubiginol, etc. which react positively with ferric sulfate, were extracted from the reaction mixture by an organic solvent such as ether.

The yield of γ-pyrone derivatives was negligibly influenced by reaction conditions. For example, a 5% aqueous solution of gluconic acid (I) was heated at 120° C. for about 30 minutes. The ratios of products formed are shown below:

Comenic acid: Rubiginic acid: Pyromeconic acid: Rubiginol: Other ferric sulfate-positves=70:9.4:5.4:5.4:9.4.

In addition, a reaction product composed of a large portion of comenic acid and a trace of other γ-pyrone derivatives was produced by heating at 50° C. for several days.

Quantitative analysis of γ-pyrone derivatives was performed according to the kojic acid colorimetric method (Ishige et al, Nippon Nogeikagakukaishi 46 353–358 (1966)). The total amount of γ-pyrone (equal to comenic acid) was calculated from the optical density measured at 500 mμ by a spectrophotometer. Color formation was determined as follows:

One half milliliter of the test sample (containing γ-pyrone derivatives) is successively treated in a tube with 1.2 ml. of 10% sulfuric acid, 0.4 ml. of 5% ferric sulfate and 2.9 ml. of distilled water. The ratio of the amount of each γ-pyrone derivative was calculated by comparison with the value which was measured by the above-described colorimetric analysis, comparing the spots separated on a paper chromatogram obtained from the reaction mixture.

Comenic acid (II) was easily separated in a pure state from the other γ-pyrone derivatives by recrystallization from water, since comenic acid (II) has a much different solubility. In view of the above fact, extracts containing comenic acid and other γ-pyrone derivatives can be dissolved with water by heating, treated with charcoal, filtered under suction while kept warm, and the filtrate condensed under reduced pressure. Comenic acid then crystallizes. The recrystallization of comenic acid from water gives a pure plate or rosette crystal melting at 276° C. The crystal obtained is identical with standard comenic acid (produced by other preparation methods) in elementary analysis, UV spectrum analysis, IR spectrum analysis and mixed melting tests.

BRIEF DESCRIPTION OF THE DRAWINGS

The drawing accompanying this application illustrates the results attained with the process disclosed herein, when the pH remains below 0.1 versus that when the pH exceeds the same. The drawing shows the production rate of γ-pyrone derivatives from a 5.0% aqueous solution of 2.5-diketogluconic acid as a function of temperature, time and initial pH of the solution in accordance with the general procedures set forth herein. The ratio of γ-pyrone derivatives generally obtained is set forth at page 4 hereof. It will be seen that the production of γ-pyrone derivatives goes through a minimum at a pH between 0.1 and 1.0 and rises rapidly at pH's below 0.1.

As described above, the method of preparing comenic acid is simple, useful in industry, and furthermore has the great advantage of high yields. The following examples illustrate the invention.

EXAMPLE 1

To 100 ml of culture medium consisting of the following components, 5 ml of a precultivated innocuum of *Acetobacter fragum* n. sp (ATCC No. 21409) was seeded:

| | | |
|---|---|---|
| Glucose | 10. | (g) |
| $(NH_4)_2SO_4$ | 0.1 | (g) |
| $KH_2PO_4$ | 0.05 | (g) |
| $K_2HPO_4$ | 0.05 | (g) |
| $MgSO_4$ | 0.02 | (g) |
| $CaCO_3$ | 2.5 | (g) |
| Nicotinamide | 100 | (δ%) |
| Calcium pantothenate | 100 | (δ%) |
| P-amino-benzoic acid | 100 | (δ%) |
| Water | Ad. 100 ml | |

The culture was incubated under shaking for 2 days. After incubation, the microorganism was removed from the fermentation liquor by centrifuge to yield an aqueous solution containing 2,5-diketo-gluconic acid (about 8.5%). To 375 ml of the solution of 2,5-diketo-gluconic acid thus prepared, 120 ml of concentrated hydrochloric acid was added and a volume of 500 ml was reacted with the addition of water (10% HCl solution). The solution was heated at 60° C. for 40 hours. After cooling, most of the comenic acid was precipitated out. The crystals were collected by filtration, washed with a small amount of water and dried to give 13.30 g of crude comenic acid (purity: 95.3%) and when the mother liquid was concentrated under reduced pressure, a further 5.39 g of comenic acid (purity: 87.2%) was obtained. Recrystallization of those crystals from water gave 16.75 g (yield 61.3%) of plate or rosette crystals of comenic acid (purity: over 98%, mp 276° C.).

EXAMPLE II

To 28 g of calcium 2,5-diketo-gluconate (purity: 71.4% calculated by Katynelson's reduction method) 180 ml of concentrated hydrochloric acid (35%) was added to make a volume of 200 ml with water. The solution of 2,5-diketo-gluconic acid (10% solution) was heated at 50° C. for 20 hours. To the reaction solution 100 ml of water was added to crystallize out 10.28 g of crude comenic acid, which was collected by filtration and when the mother liquid was concentrated under reduced pressure a further 2.34 g of crude comenic acid was obtained. Recrystallization of those crystals from water gave 10.0 g (Yield: 70.4%) of plate or rosette crystals of comenic acid (purity: over 96%).

EXAMPLE III 28 g of calcium 2,5-diketo-gluconate (purity: about 71.4% calculated by Katynelson's reduction method) was dissolved in water and a cation exchange resin (Amberlite IR-120) was added to the solution for desalting. The resin was filtered off and gaseous hydrochloric acid was introduced into the filtrate to make a 35% concentration of hydrochloric acid. The strongly acidic solution (HCl: 35%, 2,5-K.G.:*** about 10%) was kept at 8° C. for 15 days. After the reaction which was carried out in a similar manner to that of Example 2, ? ?6 g of comenic acid (purity: over 96%, yield 62%) was obtained.

For comparison purposes, the table set out below distinctly demonstrates the unexpected results attained in the process claimed, when the pH is below 0.1 versus that when the pH exceeds this parameter.

TABLE I

| | Preceding Application Serial No. 784,171 | Present Invention | Additional Example | | |
|---|---|---|---|---|---|
| | | | (1) | (2) | (3) |
| Heating Temp. (°C.) | 20–200 (50–120) | 8–120 (50–60) | 50 | 60 | 8 |

TABLE I-continued

|  | Preceding Application Serial No. 784,171 | Present Invention | Additional Example | | |
|---|---|---|---|---|---|
|  |  |  | (1) | (2) | (3) |
| Time | 30 min. to several days | over 20 hours | 40 hours | 20 hours | 15 days |
| Concentration of 2,5-K.G. (%)*** | 1–30 | 1–30 (5–15) | 8.4 | 10 | 10 |
| Initial pH | 1–7 (2–4) | below 0.1* | 10%** | 30%** | 35%** |
| Yield (%) calculated from 2,5-K.G.*** | 45 | 60–70 | 61.3 | 70.44 | 62 |

*Corresponding to over 10% expressed by concentration of HCl.
**Expressed by concentration of HCl in reaction solution
***Diketo-gluconic acid.

To further define the invention, when a carbonate is utilized, it may be present in an amount of from about 1 to about 5 weight percent (total weight). The "catalyst" (ferrous, ferric, nickel and cobalt salts) is generally present in an amount of from about 0.01 to about 1 milligrams.

When a fermentation liquor is utilized, the gluconic acid concentration therein has generally been found to be from about 1 to about 30 percent by weight.

To further define the "heating time" of the present invention, this time pertains to a period of 20 hours or more with temperature conditions being from about 8° to about 120° C., 50°–60° C. being preferred.

The percent symbols utilized in the specification imply percent by weight. Of course this would apply to the examples and the claims.

In addition to HCl, $H_2SO_4$ and $H_3PO_4$ may be employed with equal results, or any other mineral acid capable of maintaining a pH below 0.1.

Although the present invention has been adequately set forth in the above disclosure and Examples included therein, it is readily apparent that various changes and modifications can be made without departing from the spirit and scope thereof.

What is claimed is:

1. A method of preparing comenic acid, which comprises acidifying an aqueous solution of 2,5-diketo-gluconic acid, or its alkali metal or alkaline earth metal salt, with hydrochloric acid and heating the resulting mixture to within a range of from about 50° to 60° C., the pH of said mixture being below 0.1.

2. The method of claim 1 in which the concentration of the aqueous solution of 2,5-diketo-gluconic acid is from 1 to 30% by weight.

3. The method of claim 2, wherein said concentration ranges from 5–15% by weight.

4. The method of claim 1 wherein said aqueous solution of 2,5-diketo-gluconic acid is a fermentation liquor derived from culturing a microorganism capable of producing 2,5-diketo-gluconic acid, said liquor being separated from the ferment organism and containing the 2,5-diketo-gluconic acid.

* * * * *